(12) United States Patent
Pendse et al.

(10) Patent No.: US 12,226,399 B2
(45) Date of Patent: Feb. 18, 2025

(54) ORAL AQUEOUS SUSPENSION FORMULATION COMPRISING CARBAMATE COMPOUND

(71) Applicant: SK BIOPHARMACEUTICALS CO., LTD., Gyeonggi-do (KR)

(72) Inventors: Pravada Pendse, Lake Hopatcong, NJ (US); Murali M Bommana, Monroe Township, NJ (US); Regina H. Noh, Hackensack, NJ (US); Augustin Pegan, Riverdale, NJ (US); Travis John Webb, St. Petersburg, FL (US); Jejuan Maxwell, Clearwater, FL (US)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 0 days.

(21) Appl. No.: 17/826,289

(22) Filed: May 27, 2022

(65) Prior Publication Data

US 2023/0013175 A1   Jan. 19, 2023

Related U.S. Application Data

(60) Provisional application No. 63/194,276, filed on May 28, 2021.

(51) Int. Cl.
| | | |
|---|---|---|
| *A61K 31/41* | (2006.01) | |
| *A61K 9/10* | (2006.01) | |
| *A61K 47/02* | (2006.01) | |
| *A61K 47/10* | (2017.01) | |
| *A61K 47/32* | (2006.01) | |
| *A61K 47/34* | (2017.01) | |
| *A61K 47/36* | (2006.01) | |
| *A61K 47/38* | (2006.01) | |
| *A61P 25/00* | (2006.01) | |

(52) U.S. Cl.
CPC ............... *A61K 31/41* (2013.01); *A61K 9/10* (2013.01); *A61K 47/02* (2013.01); *A61K 47/10* (2013.01); *A61K 47/32* (2013.01); *A61K 47/38* (2013.01)

(58) Field of Classification Search
CPC ............ A61K 31/41; A61K 9/10; A61K 4/02; A61K 4/10; A61K 4/32; A61K 4/38; A61K 4/36; A61K 4/34; A61P 25/00
See application file for complete search history.

(56) References Cited

U.S. PATENT DOCUMENTS

2022/0117941 A1* 4/2022 Ryu ..................... A61P 25/22
2023/0157947 A1* 5/2023 Lee ..................... A61K 9/2018
                                                           424/489

FOREIGN PATENT DOCUMENTS

| WO | WO-2006/112685 A1 | 10/2006 |
| WO | WO-2010/150946 A1 | 12/2010 |
| WO | WO-2011/046380 A2 | 4/2011 |

* cited by examiner

*Primary Examiner* — Sun Jae Yoo
(74) *Attorney, Agent, or Firm* — Harness, Dickey & Pierce, P.L.C.

(57) ABSTRACT

The present disclosure relates to an aqueous formulation comprising as an active ingredient a carbamate compound of Formula 1, or a pharmaceutically acceptable salt, solvate or hydrate thereof, poloxamer, and an aqueous carrier, wherein the aqueous formulation is in the form of a suspension formulation.

30 Claims, 6 Drawing Sheets

(A: 10 min, B: 5hr, C: 24hr; Left to right: 0.10, 0.50, 1.00, and 1.50 mg/mL poloxamer 188)

(A: 10 min, B: 4 hr, C: 24 hr; Left to right: at pH 3.5, 4.2 and 6.2, 0.1 mg/mL of poloxamer 188)

ORAL AQUEOUS SUSPENSION FORMULATION COMPRISING CARBAMATE COMPOUND

CROSS-REFERENCE TO RELATED APPLICATIONS

This application claims the benefit of U.S. Patent Application No. 63/194,276, filed on May 28, 2021. The entire disclosure of the application identified in this paragraph is incorporated herein by reference.

FIELD

The present disclosure relates generally to a pharmaceutical composition and a method of using the same, and more particularly to an aqueous formulation comprising a carbamate compound of Formula 1, or a pharmaceutically acceptable salt, solvate or hydrate thereof; and poloxamer:

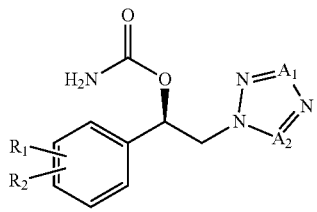

[Formula 1]

wherein, $R_1$, $R_2$, $A_1$ and $A_2$ are as defined herein.

BACKGROUND

PCT Publication Nos. WO 2006/112685 $A_1$, WO 2010/150946 $A_1$ and WO 2011/046380 $A_2$ describe the carbamate compounds of Formula 1 and methods for preparing the same, and the disclosures of the patent publications are incorporated herein by reference. In one specific embodiment, the carbamate compound of Formula 1 is carbamic acid (R)-1-(2-chlorophenyl)-2-tetrazol-2-yl-ethyl ester having the chemical structure of Formula 2:

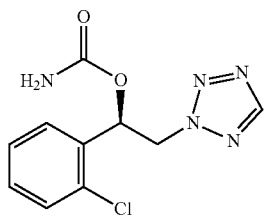

[Formula 2]

The carbamate compounds of Formula 1 are known to be effective anticonvulsants for use in central nervous system diseases.

Formulations comprising the compounds are suitable for repeated administration over an extended treatment period to ensure a uniform concentration of active ingredient in the blood. However, solid oral dosage formulations such as capsules or tablets are usually intended for adults who can easily swallow large tablets. As such, there is a need to develop a formulation that can be easily administered to patients who have difficulty in swallowing capsules or tablets—e.g., pediatric patients and adults with difficulty in swallowing and using in GI tube, etc.

SUMMARY

Because of the ease of preparing solid dosage forms, tablets and capsules are preferred dosage form and currently the FDA approved cenobamate (carbamate compound under this discussion) product is in solid dosage form, i.e. tablets. There is an unmet need to have suitable oral liquid cenobamate formulation as an additional treatment option mainly for pediatric and geriatric population. Liquid dosage forms present more challenge because of solubility and stability in presence of various excipients and solvents in case of solution and for physical stability in case of oral suspensions. The present disclosure addresses, in part, physical stability issues for an oral suspension. Liquid dosage forms also pose challenges regarding screening for suitable sweetener and flavoring agent to make the formulation more palatable to the population under consideration. These attributes are intended to increase patient compliance. The specific combination of sweetener, flavor and bitter masking agent needs to be selected by taste testing various combinations to solve the issue of the bitter taste of the compound. The formulation needs suitable preservatives due to its aqueous nature within the limits allowable for pediatric population. In addition, the buffer system should present optimum pH for preservative efficacy and also overall formulation stability. Accordingly, in various embodiments, the present disclosure provides an oral aqueous suspension formulation comprising the carbamate compounds of Formula 1 or 2 as an active ingredient, wherein said formulation has controlled and optimum solubility to enable undissolved particles suspended in aqueous buffer system and excellent storage stability of the active ingredient. Crystal growth potential due to exceeding saturation solubility and bitter taste are intended to be overcome by specific formulation strategies.

The present disclosure provides an aqueous formulation comprising as an active ingredient a carbamate compound of Formula 1, or a pharmaceutically acceptable salt, solvate or hydrate thereof, poloxamer, and an aqueous carrier:

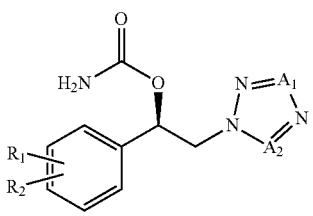

[Formula 1]

wherein,
$R_1$ and $R_2$ are each independently selected from the group consisting of —H, halo, $C_1$-$C_8$ alkyl, halo-$C_1$-$C_8$ alkyl, $C_1$-$C_8$ thioalkoxy, and $C_1$-$C_8$ alkoxy; and
one of $A_1$ and $A_2$ is CH, and the other is N,
wherein the formulation is in the form of a suspension formulation.

The present disclosure also provides an aqueous formulation comprising as an active ingredient a carbamate compound of Formula 1, or a pharmaceutically acceptable salt, solvate or hydrate thereof, smectite clay, and an aqueous carrier, wherein the formulation is in the form of a suspension formulation.

The present disclosure also provides an aqueous formulation described herein, for use as an anticonvulsant.

According to one embodiment, the aqueous formulation is used for the treatment of central nervous system diseases such as anxiety, depression, convulsion, epilepsy, migraine, bipolar disorder, drug abuse, smoking, attention deficit hyperactivity disorder (ADHD), obesity, sleep disorders, neuropathic pain, stroke, cognitive disorders, neurodegeneration, and/or muscle spasm.

The aqueous suspension according to the present disclosure can uniformly disperse and suspend the active compound in a structured vehicle, with excellent physical and chemical stability upon storage. The structured vehicle may be formulated to provide a system of aqueous buffer, a surfactant, and/or one or more viscosity modifiers to control viscosity, pH and/or the particle size of the active compound in the formulation. In some embodiments, the present formulations resolve the bitter taste associated with the active compound optionally using a combination of a suitable sweetener, a bitter masking agent, and/or a flavoring agent. In some embodiment, the formulation comprises a preservative proven by appropriate antimicrobial effectiveness testing at levels up to 75% and 85% of the desired level to have the antimicrobial effectiveness in the formulation.

In particular embodiments, poloxamer is included with the active compound in a suspension formulation for wide pH range even in low concentrations. In some embodiments, smectite clay shows a synergistic effect on redispersibility/suspendability of a suspension formulation with a cellulosic viscosity modifier or xanthan gum.

DETAILED DESCRIPTION

Figure 1:
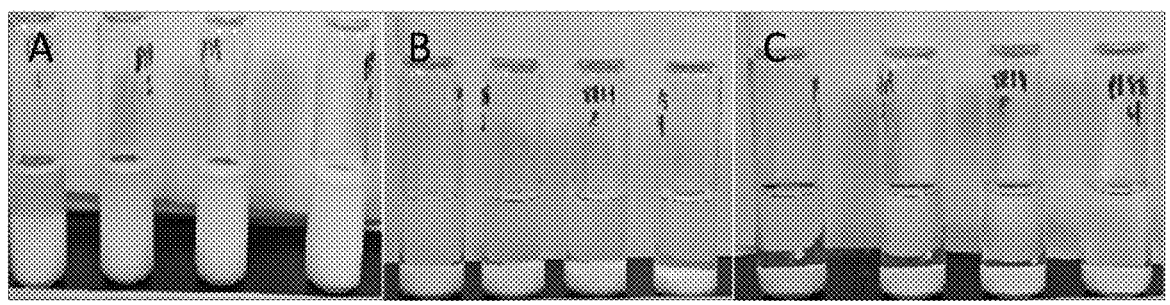
FIG. 1 shows images of sedimentation pattern of cenobamate containing different concentrations of poloxamer 188 in phosphate buffer.

Hereinafter, the present disclosure will be described in detail.

An oral suspension can be selected as a formulation of choice amongst oral liquids. Oral suspension is advantageous to have the active ingredient in a particulate form and not solubilized beyond its saturation solubility using a co-solvent and thereby presenting less potential for crystal growth of the active ingredient as compared to the solution. The dosage form needs to have less amount of active ingredient in dissolved state thereby helping to reduce bitter taste.

The present disclosure provides an aqueous formulation comprising as an active ingredient a carbamate compound of Formula 1, or a pharmaceutically acceptable salt, solvate or hydrate thereof, poloxamer, and an aqueous carrier:

[Formula 1]

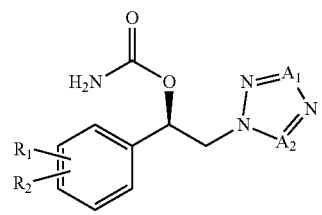

wherein, $R_1$ and $R_2$ are each independently selected from the group consisting of —H, halo, $C_1$-$C_8$ alkyl, halo-$C_1$-$C_8$ alkyl, $C_1$-$C_8$ thioalkoxy, and $C_1$-$C_8$ alkoxy;

one of $A_1$ and $A_2$ is CH, and the other is N, wherein the formulation is in the form of a suspension formulation. In an embodiment, the aqueous formulation is a formulation for oral administration.

In one embodiment, in Formula 1, $R_1$ and $R_2$ are each independently selected from the group consisting of —H, halo, and $C_1$-$C_8$ alkyl.

In one embodiment, the halo $C_1$-$C_8$ alkyl is perfluoroalkyl.

In one embodiment, the carbamate compound of Formula 1 is carbamic acid (R)-1-(2-chlorophenyl)-2-tetrazol-2-yl-ethyl ester of Formula 2:

[Formula 2]

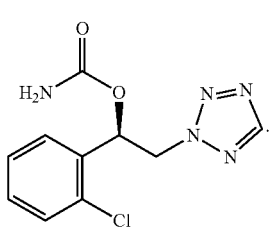

The carbamic acid (R)-1-(2-chlorophenyl)-2-tetrazol-2-yl-ethyl ester of Formula 2, cenobamate, is an antiepileptic drug for the treatment of partial-onset seizures and known to reduce neuronal excitability by blocking the inactivate state of voltage-gated sodium channels and the increase of inhibitory effects of γ aminobutyric acid (GABA) system by enhancing the presynaptic release of GABA.

The term "compound" or "active ingredient" is a concept that encompasses not only the compound itself but also its isomers, or pharmaceutically acceptable salts, solvates and hydrates thereof altogether. Accordingly, as used herein, the carbamate compound of Formula 1 refers to not only the compound but also its isomers, or pharmaceutically acceptable salts, solvates or hydrates thereof. Likewise, as used herein, the carbamate compound of Formula 2 refers to not only the carbamic acid (R)-1-(2-chlorophenyl)-2-tetrazol-2-ylethyl ester but also its isomers, or pharmaceutically acceptable salts, solvates or hydrates thereof.

Examples of the pharmaceutically acceptable salts of the carbamate compounds of Formula 1 include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate, hydravamine, hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemi-succinate, sulfate or hemi-sulfate, tannate, tartrate, oxalate or hemi-tartrate, teoclate, procaine, aluminum, ammonium, tetramethylammonium, calcium, lithium, magnesium, potassium, sodium and zinc.

A person having ordinary skill in the art of synthesis of compounds could have easily prepared the carbamate compounds of Formulas 1 and 2 using known compounds or compounds which can be easily prepared therefrom. In particular, methods for preparing the compounds of Formula 1 are described in detail in PCT Publication Nos. WO 2006/112685 A1, WO 2010/150946 A1 and WO 2011/046380 A2, the disclosures of which are incorporated herein by reference. The compounds of Formula 1 can be chemically synthesized by any of the methods described in the above documents, but the methods are merely exemplary ones, and the order of the unit operation and the like may be selectively changed if necessary. Hence, the above methods are not intended to limit the scope of the invention.

The content of the carbamate compounds of Formula 1 or 2 in the oral aqueous suspension formulation may vary depending on the application of the preparation. In one embodiment, the oral aqueous suspension formulation contains the carbamate compounds of Formula 1 or 2 in a concentration of about 1 mg/ml to about 100 mg/ml. In one embodiment, the oral aqueous suspension formulation contains the carbamate compounds of Formula 1 or 2 in a concentration of about 1 mg/ml to about 50 mg/ml. In one embodiment, the oral aqueous suspension formulation contains the carbamate compounds of Formula 1 or 2 in a concentration of about 5 mg/ml to about 20 mg/ml. In one embodiment, the oral aqueous suspension formulation contains the carbamate compounds of Formula 1 or 2 in a concentration of about 5 mg/ml to about 12 mg/ml. In one embodiment, the oral aqueous suspension formulation contains the carbamate compounds of Formula 1 or 2 in a concentration of about 8 mg/ml to about 12 mg/ml. In one embodiment, the oral aqueous suspension formulation contains the carbamate compounds of Formula 1 or 2 in a concentration of about 9 mg/ml to about 11 mg/ml.

In various embodiments, a pharmaceutical composition in the form of a suspension comprises a carbamate compound or its pharmaceutically acceptable salts with one or more pharmaceutically acceptable excipient and an aqueous carrier. The aqueous carrier is selected from the group comprising water, and a mixture of water and a water-miscible organic solvent. In one embodiment, said organic solvents are selected from the group consisting of ethanol, ethylene bromide, butanol, acetone, chloroform, 2-ethylhexanol, methyl ethyl ketone, ethylene chloride, isobutanol, glycerol, methyl isobutyl ketone, dichloromethane, isopropanol, methyl isopropyl ketone, tetrachloroethylene, methanol, mesityl oxide, carbon tetrachloride, propanol, trichloroethylene, propylene glycol, 1,4-dioxane, butyl ether, dimethylformamide, ethyl ether, diisopropyl ether, dimethyl sulfoxide, tetrahydrofuran, tert-butyl methyl ether, pyridyne, acetonitrile, ethyl acetate, cyclohexane, toluene, hexane, xylene, other suitable solvents, and combinations thereof. In another embodiment, the aqueous carrier includes water, water buffered to a specific pH with phosphate or carbonate ions, and combinations of aqueous and one or more organic solvents. In a particular embodiment, the aqueous carrier is water. In some embodiments, the aqueous formulation comprises an aqueous carrier in an amount of from 40% to 99%, from 70% to 98%, or from 90% to 95%, by weight of the formulation.

In one embodiment, the poloxamer is an ABA block type copolymer which consists of 75 to 85% polyoxyethylene (PEO) units and 15 to 25% polyoxypropylene (PPO) units. In one embodiment, the poloxamer is an ABA block type copolymer which consists of about 80% polyoxyethylene (PEO) units of A block and about 20% polyoxypropylene (PPO) units of B block. In one embodiment, the poloxamer is poloxamer 188 (P188). In one embodiment, the aqueous formulation contains poloxamer in a concentration of about 0.1 mg/ml to about 1.5 mg/ml. In one embodiment, the aqueous formulation contains poloxamer in a concentration of about 0.8 mg/ml to about 1.2 mg/ml. In one embodiment, the aqueous formulation contains poloxamer in a concentration of about 0.1 mg/ml to about 0.5 mg/ml. In some embodiments, poloxamer is added to provide sufficient spacing of the settled particles of the active ingredient and to permit the active ingredient to re-disperse with minimal effort at a wide range of pH and regardless of the type of buffer.

In one embodiment, the aqueous formulation further comprises smectite clay. Smectite clay can be added as a suspending agent to the aqueous formulation to improve its suspending and viscosity properties. Smectite clay could prevent settling the particles of the active ingredient and imparts the viscosity to the formulation. In one embodiment, the smectite clay is selected from the group consisting of aluminum silicates such as montmorillonites (bentonites, hectorites and derivatives thereof); magnesium aluminum silicates (various grades are commercially available as Veegum® from R. T. Vanderbilt Company); sodium magnesium silicates (commercially available as Laponite® in varying degrees); organically modified smectites including tetra alkyl and/or trialkyl ammonium smectites (organically modified clays) such as quaternary-18 bentonite, quaternary-18 hectorite, stearalkonium bentonite and stearalkonium hectorite, and mixtures thereof. In one embodiment, the smectite clay is a purified one. In one embodiment, the smectite clay is magnesium aluminum silicate. The smectite clay may be specifically magnesium aluminum silicate type IC, and more specifically, the smectite clay may be Veegum HV, Veegum R, Veegum K, or any combination thereof. In one embodiment, the aqueous formulation contains smectite clay in a concentration of about 2.5 mg/ml to about 7.0 mg/ml. In one embodiment, the aqueous formulation contains smectite clay in a concentration of about 4 mg/ml to about 6 mg/ml. A specific grade may be required for viscosity building of the suspension with low solid content and needs grade or quantity modification based on desired concentration and solid content of final formulation.

In one embodiment, the aqueous formulation further comprises a viscosity modifier. The viscosity modifier can be added to reduce the settling rate of the particles in the formulation. Viscosity modifiers may be used synergistically in combination with one or more excipients hereof to improve suspendability and re-dispersibility of the formulation. In one embodiment, the aqueous formulation contains the viscosity modifier in a concentration of about 1 mg/mL to about 25 mg/ml. The viscosity modifier that is considered to have synergistic effects with smectite clays may be selected. In one embodiment, a viscosity modifier maybe a recrystallization inhibitor as seen from PSD data.

In one embodiment, the viscosity modifier is selected from the group consisting of cellulose or a derivative thereof, and xanthan gum. In one embodiment, the aqueous formulation contains the xanthan gum in a concentration of about 1 mg/ml to about 10 mg/ml, about 2 mg/ml to about 6 mg/ml, or about 3 mg/ml to about 5 mg/ml. In one embodiment, the viscosity modifier is cellulose or a derivative thereof. In one embodiment, the cellulose derivative is selected from the group consisting of methyl cellulose (MC), ethyl cellulose (EC), hydroxyethylcellulose (HEC), hydroxypropyl cellulose (HPC), hydroxypropyl methylcellulose (HPMC), carboxymethyl cellulose (CMC), microcrystalline cellulose (MCC), cellulose acetate (CA), cellulose acetate phthalate (CAP), cellulose acetate butyrate (CAB), cellulose acetate trimelitate (CAT), hydroxupropylmethyl cellulose phthalate (HPMCP) and a combination thereof. In one embodiment, the mixture of carboxymethyl cellulose (CMC) and microcrystalline cellulose (MCC) is selected. In one embodiment, the aqueous formulation contains cellulose or derivative in a concentration of about 1 mg/mL to about 25 mg/ml. In one embodiment, the aqueous formulation contains cellulose or derivative thereof in a concentration of about 15 mg/ml to about 25 mg/mL or about 15 mg/ml to about 20 mg/mL. In one embodiment, the aqueous formulation contains cellulose or derivative thereof in a concentration of about 5 mg/ml to about 14 ml or about 8 mg/ml to about 12 mg/ml In one embodiment, the aqueous formulation further comprises a sweetener. In one embodiment, the sweetener is selected from the group consisting of sorbitol, mannitol, maltitol, xylitol and a mixture thereof. In one embodiment, the oral aqueous formulation contains the sweetener in a concentration of about 10 mg/ml to about 30 mg/ml. In one embodiment, the sweetener may function as recrystallization and cryoprotectant and ensure the consistency of the formulation. In one embodiment a formulation comprises suitable combination of a sweetener, a bitter masker and a flavoring agent evaluated to overcome the bitterness of the active ingredient wherever applicable. In one embodiment, the sweetener is selected from a group consisting of a sugar alcohol, substituted disaccharide derivative, and salts of glycyrrhizic acid. In this regard, the sweetener is used in combination with a flavoring agent such as raspberry, cherry, peppermint, orange, strawberry, grape, black cherry, and apple.

In one embodiment, the aqueous formulation further comprises one or more of a recrystallization inhibitor, a flavoring agent, a bitter masker, a preservative, and a buffer. In one embodiment, the recrystallization inhibitor is polyvinylpyrrolidone (PVP) or hydroxypropyl methylcellulose (HPMC). In one embodiment, the aqueous formulation contains polyvinylpyrrolidone (PVP) in a concentration of about 20 mg/ml to about 40 mg/ml. In one embodiment, the aqueous formulation contains hydroxypropyl methylcellulose (HPMC) in a concentration of about 1 mg/ml to about 5 mg/ml. In one embodiment, the buffer is a citrate buffer or a phosphate buffer.

In one embodiment, the aqueous suspension comprises at least one preservative, in particular chosen from the group consisting of parahydroxybenzoic acid, benzoic acid, boric acid, sorbic acid, their salts, and a combination thereof, more preferably sodium benzoate, in a concentration of about 0.5 mg/ml to about 5.0 mg/mL or about 1.0 mg/ml to about 2.0 mg/mL, or about 1.3 mg/ml to about 1.7 mg/mL. In one embodiment, the aqueous suspension is stable for or more twelve months at 25° C./60% RH and 40° C./75% RH. In one embodiment, the aqueous suspension is stable for or more eighteen months at 25° C./60% RH and 40° C./75% RH. In one embodiment, the aqueous formulation may comprise the carbamate compound of Formula 1 or 2 within the following particle sizes distribution of the carbamate compound of Formula 1 or 2: D10 is 1 to 15 µm, 1.4 to 10 µm or 1.5 to 5 µm, more specifically, 1 to 3 µm, 1.5 to 3 µm, 3 to 6 µm, 6 to 9 µm, 9 to 12 µm, 12 to 15 µm. In one embodiment, the aqueous formulation may comprise the carbamate compound of Formula 1 or 2 within the following particle sizes distribution of the carbamate compound of Formula 1 or 2: D50 is 1 to 20 µm, 1 to 15 µm or 5 to 10 µm, more specifically, 1.5 to 3 µm, 3 to 6 µm, 4 to 9 µm, 5 to 9 µm, 6 to 9 µm, 9 to 12 µm, 12 to 15 µm, 15 to 18 µm, 18 to 20 µm. In one embodiment, the aqueous formulation may comprise the carbamate compound of Formula 1 or 2 within the following particle sizes distribution of the carbamate compound of Formula 1 or 2: D90 is 1 to 60 µm, 5 to 50 µm, or 10 to 45 µm, more specifically, 10 to 15 µm, 10 to 20 µm, 20 to 30 µm, 30 to 45 µm, or 40 to 50 µm. In one embodiment, the particle size of the carbamate compound of Formula 1 or 2 can be controlled by a milling process or other available processes. In one embodiment, the aqueous formulation comprises the carbamate compound of Formula 1 or 2 having the above ranges of particle size distribution to give the uniformity to the oral aqueous suspension formulation.

In one embodiment, the particle sizes of the carbamate compound of Formula 1 or 2 which could be used to prepare the oral aqueous formulation are as following: D10 is 1 to 30 µm, 1.4 to 28 µm or 1.5 to 27 µm, more specifically, 1.5 to 3 µm, 3 to 6 µm, 6 to 9 µm, 9 to 12 µm, 12 to 15 µm, 15 to 18 µm, 18 to 21 µm, 21 to 24 µm, or 24 to 27 µm. In one embodiment, the particle sizes of the carbamate compound of Formula 1 or 2 which could be used to prepare the oral aqueous formulation are as following: D50 is 3 to 60 µm, 3.2 to 58 µm or 3.5 to 55 µm, more specifically, 3.5 to 5.0 µm, 5.0 to 10 µm, 10 to 15 µm, 15 to 20 µm, 20 to 25 µm, 25 to 30 µm, 35 to 40 µm, 40 to 45 µm, 45 to 50 µm, or 50 to 55 µm. In one embodiment, the particle sizes of the carbamate compound of Formula 1 or 2 which could be used to prepare the oral aqueous formulation are as following: D90 is 5 to 120 µm, 7 to 110 µm or 8 to 100 µm, more specifically, 10 to 20 µm, 20 to 30 µm, 30 to 40 µm, 40 to 50 µm, 50 to 60 µm, 60 to 70 µm, 70 to 80 µm, 80 to 90 µm, or 90 to 100 µm.

As used herein, $D_{10}$, $D_{50}$ and $D_{90}$ represent the median or the $10^{th}$ percentile, $50^{th}$ percentile and the $90^{th}$ percentile of the particle size distribution, respectively, as measured by volume. This means, the term "D50" is defined as the size in microns below which 50 percent of the particles reside on a volume basis and similarly, the term "D90" is defined as the size in microns below which 90 percent of the particles reside, on a volume basis. Particle size can be determined, for example, by laser light scattering using a particle size analyser, such as the proprietary Mie scattering, Cilas 1180.

In one embodiment, the aqueous formulation has a pH of about 3.5 to about 7.0, about 3.5 to about 6.0, or about 3.5 to about 5.5.

The resulting oral suspension may be tested with suitable analytical methods to ensure physical and chemical stability. Examples of the analytical methodologies include, but is not limited to, appearance, pH, viscosity, assay and related substances, chiral purity assay, homogeneity, re-dispersibility, dissolution, particles size and XRD.

The wetting agent and viscosity modifiers may be optimized using analysis of formulations with wettability/dispersibility indicators such as sedimentation volume, re-dispersibility and wettability of powder in a water after controlled stirring and visually observing the sample for signs of caking, flocculation, and dispersibility of the compound. The volume of the sedimentation layer is an indicator to the amount of spacing between the particles in the sediment layer. Adequate spacing between the particles is essential because these particles have to move in order to disperse evenly.

In an embodiment, the aqueous formulation is used as an anticonvulsant, and can be used for the treatment of anxiety, depression, convulsion, epilepsy, migraine, bipolar disorder, drug abuse, smoking, attention deficit hyperactivity disorder (ADHD), obesity, sleep disorders, neuropathic pain, stroke, cognitive impairment, neurodegeneration and/or muscle spasm.

The dosage amount of the carbamate compounds of Formula 1 or 2 for the prevention, alleviation or treatment of the above diseases may typically vary depending on the severity of the disease, the body weight and the metabolic status of the subject. A "therapeutically effective amount" for an individual patient refers to an amount of the active ingredient sufficient to achieve a therapeutic effect. Specifically, the therapeutically effective amount of the active ingredient is 50 to 500 mg, 50 to 400 mg, 50 to 300 mg, 100 to 400 mg, 100 to 300 mg, 50 to 200 mg, or 100 to 200 mg, based on the free form and once-daily administration to humans. The therapeutically effective amount is preferably 50 to 400 mg, more preferably 50 to 200 mg.

The present disclosure provides an aqueous formulation comprising as an active ingredient a carbamate compound of Formula 1, or a pharmaceutically acceptable salt, solvate or hydrate thereof, smectite clay, and an aqueous carrier:

[Formula 1]

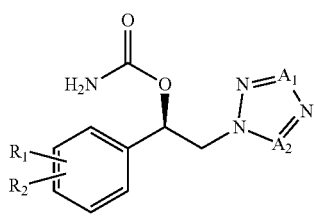

wherein, $R_1$ and $R_2$ are each independently selected from the group consisting of —H, halo, $C_1$-$C_8$ alkyl, halo-$C_1$-$C_8$ alkyl, $C_1$-$C_8$ thioalkoxy, and $C_1$-$C_8$ alkoxy;

one of $A_1$ and $A_2$ is CH, and the other is N, wherein the aqueous formulation is a suspension formulation. In an embodiment, the aqueous formulation is a formulation for oral administration.

The carbamate compound and the smectite clay are as previously described. In one embodiment, the aqueous formulation further comprises the poloxamer above-described. In one embodiment, the aqueous formulation further comprises one or more excipients as described herein.

Hereinafter, the present invention will be explained in more detail through working examples. However, the following working examples are only intended to illustrate one or more embodiments and are not intended to limit the scope of the invention.

EXAMPLES

Preparation Example: Synthesis of Carbamic Acid (R)-1-(2-chlorophenyl)-2-tetrazol-2-yl-ethyl ester The compound of Formula 2 ("cenobamate") was prepared according to the method described in Preparation Example 50 of International Publication No. WO 2010/150946.

Example 1

Figure 2:
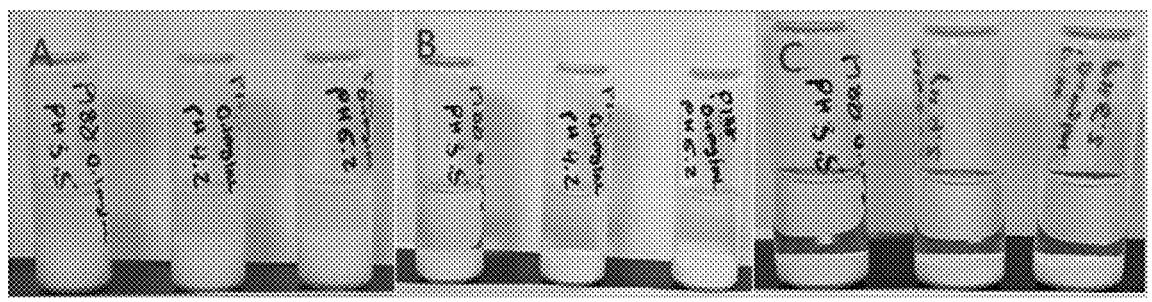
FIG. 2 shows images of sedimentation pattern of cenobamate containing poloxamer 188 0.1 mg/mL in citrate buffer.
Figure 3:
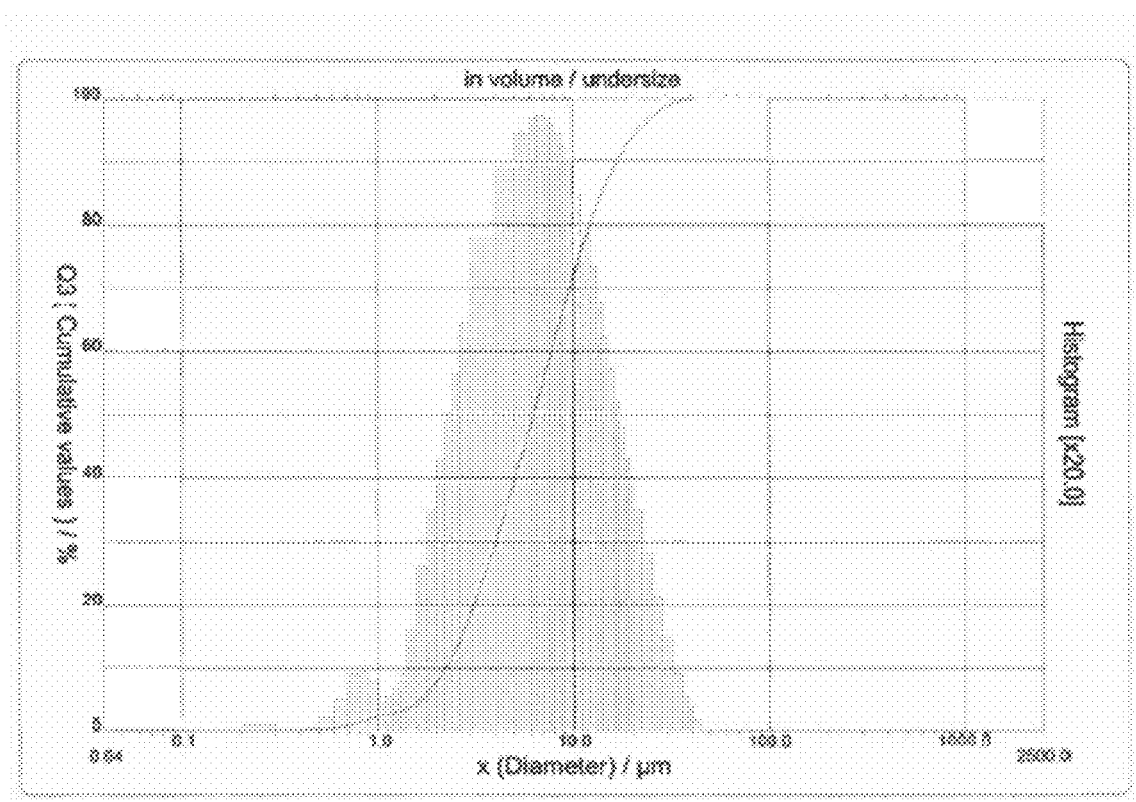
FIG. 3 is a PSD histogram of Formulation I—upright configuration at 6 month pull with 40° C./75% RH storage condition.
Figure 4:
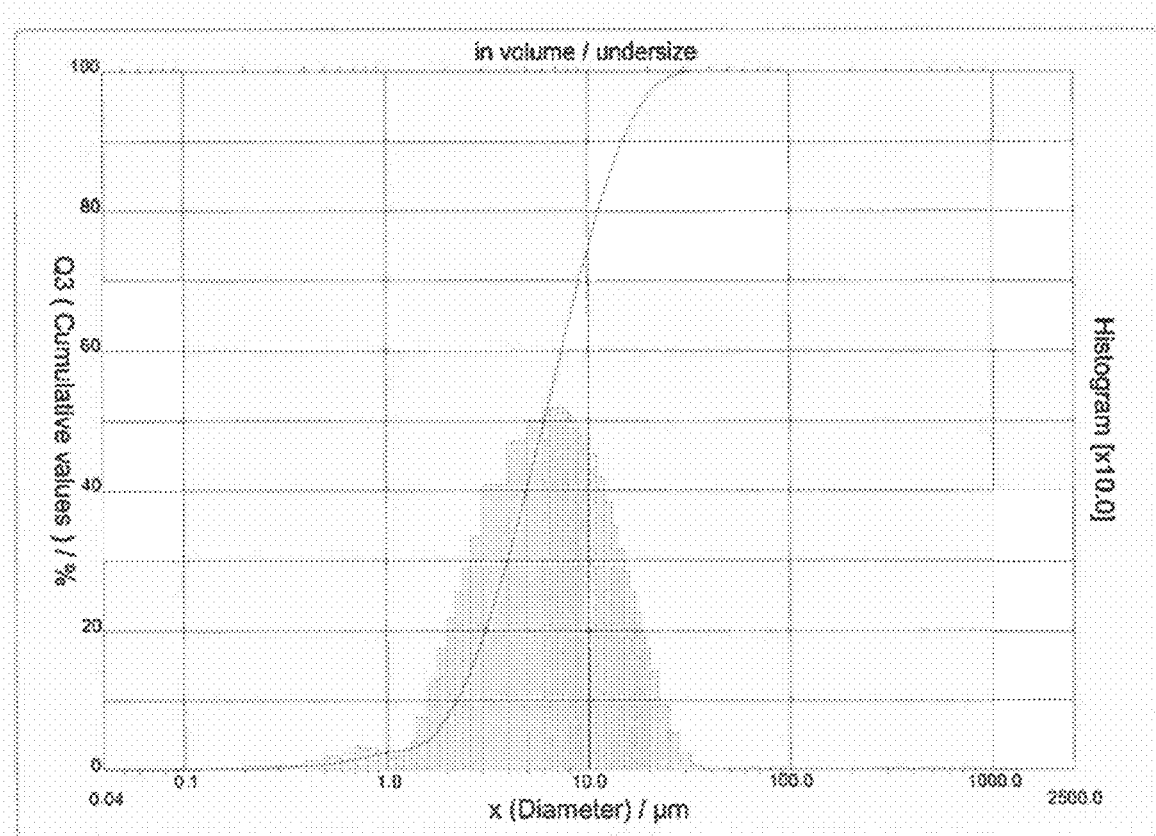
FIG. 4 is a PSD histogram of Formulation II—inverted configuration at 6 month pull with 40° C./75% RH storage condition.
Figure 5:
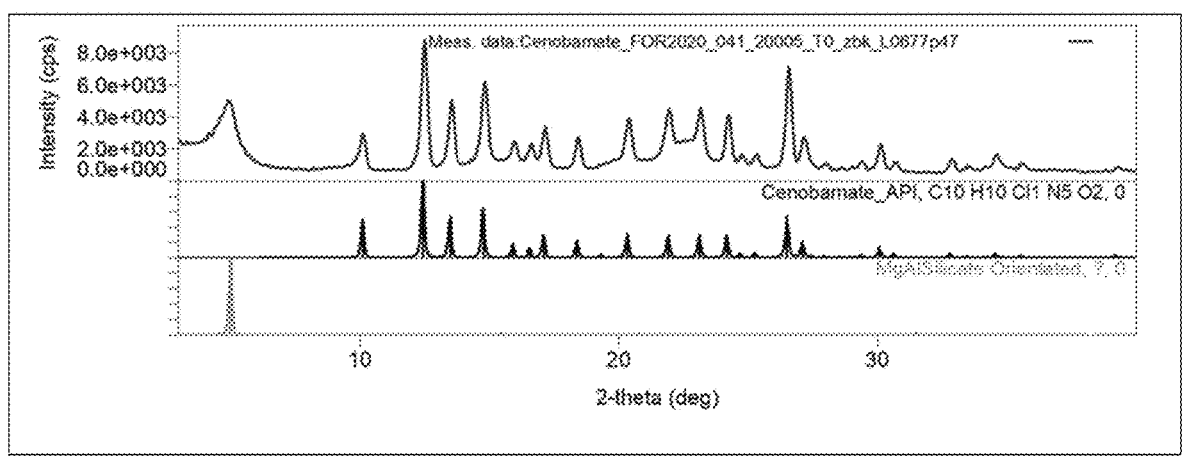
FIG. 5 shows XRD results of Formulation I at T=0.
Figure 6:
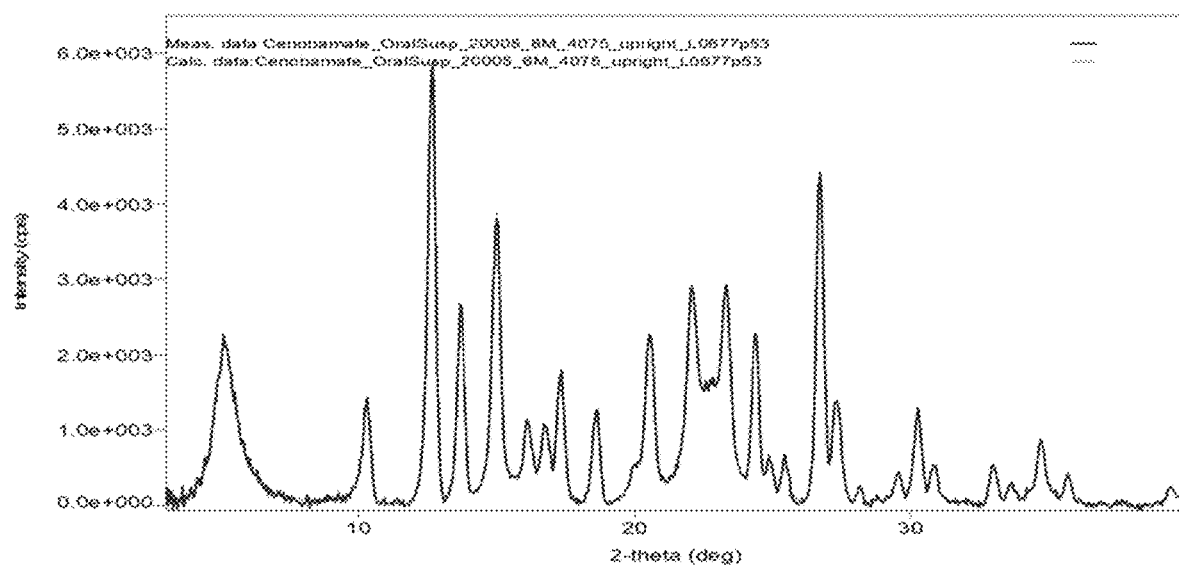
FIG. 6 shows XRD results of Formulation I—upright configuration at 6 month pull with 40 C/75% RH storage condition.
Figure 7:
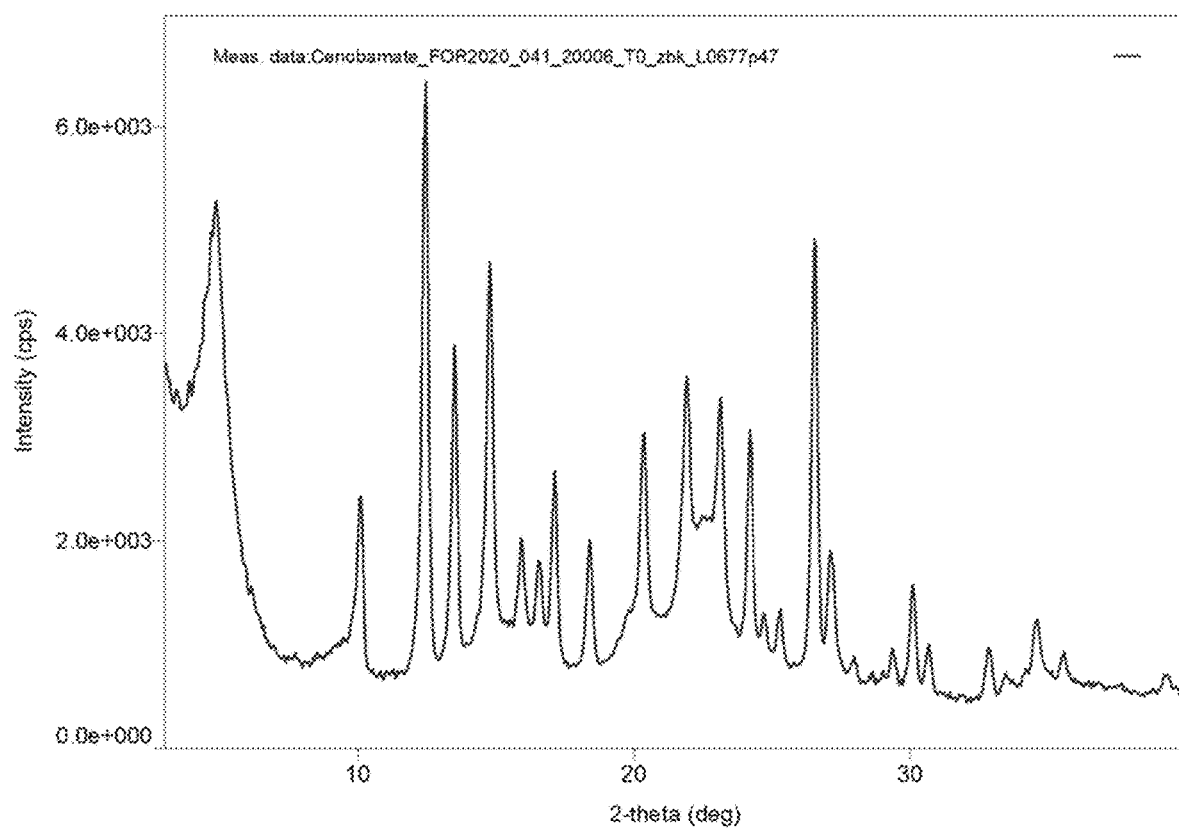
FIG. 7 shows XRD results of Formulation II at T=0.
Figure 8:
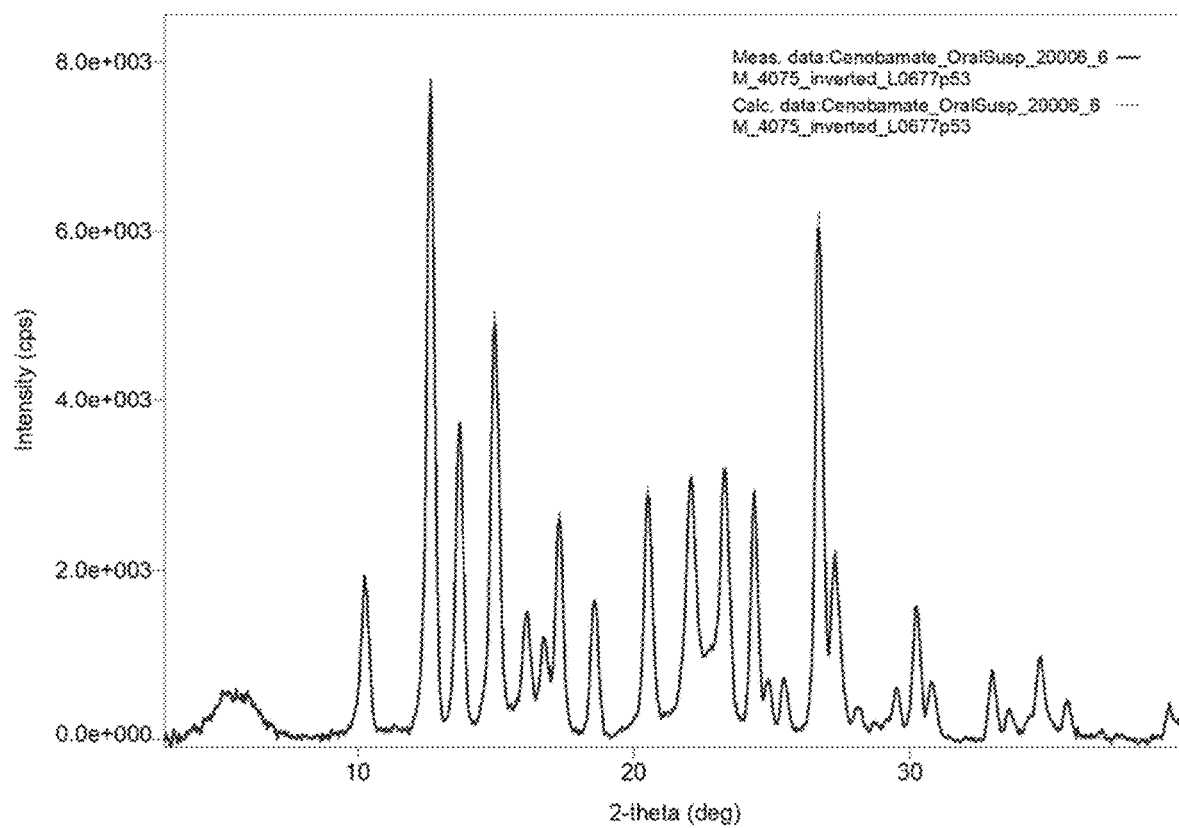
FIG. 8 shows XRD results of Formulation II-inverted configuration T=0 overlayed with 6 month pull with 40° C./75% RH storage condition.

Poloxamer 188 was evaluated at different concentrations for sedimentation volume, dispensability and wettability of cenobamate containing dispersion in a neat citrate or phosphate buffer at pH 3 to 7. Approximately one hundred milligrams (100 mg) of cenobamate was dispersed in 10 mL of the poloxamer liquid at the concentration of 0.10, 0.50, 1.00, and 1.50 mg/mL in phosphate buffer pH 4.2 and the dispersions were evaluated for sedimentation volume, re-dispersibility, and wettability. The images are shown in FIG. 1. Additionally, separate samples containing poloxamer 188 at the concertation of 0.1 mg/ml were also prepared in citrate buffer at different levels of pH (pH 3.5, 4.2 and 5.2), and evaluated in the same manner. The images are shown in FIG. 2.

The volume of the sedimentation layer is an indicator to the amount of spacing between the particles in the sediment layer. Physical observations indicated these dispersions settled rapidly but formed a loosely packed layer which was very easily re-dispersed after inversion and/or shaking (FIGS. 1 and 2). Similarly good wetting of cenobamate was observed in the presence of poloxamer 188 as evaluated by time required for cenobamate to fall below the surface.

TABLE 1

Testing matrix in different pH and buffers
Testing

| Test | Method | Description |
|---|---|---|
| Sedimentation Measurement | Visual | Measure the sediment layer and total volume to determine the sediment volume, F = Vu/Vo |
| Initial Sedimentation | Visual | Observe the formation of sedimentation |
| Sample Inversion | Visual | Invert sample and inspect for caking and redispersion |
| Wetting | Visual | Applied 30 mg of cenobamate API to the surface of 30 mL of wetting agent solution in buffer with slow mixed and observe time needed to wet all of cenobamate |
| Re-dispersion | Visual | Shake samples for 10 seconds |

The poloxamer 188 dispersions demonstrated an almost immediate flocculation and provided sufficient spacing of the settled particles to permit the drug substance to re-disperse with minimal effort within all the range between pH 3.5 and 5.2, and regardless of the buffer type. The following intended effects that were observed are immediate wetting of most of the material after adding cenobamate to the poloxamer solution, rapid and loose initial sedimentation within first 30 minutes to 1 hour as measured by ratio of sediment volume to total volume, no caking and efficient re-dispersion, rapidly dispersing material after shaking the settled sample for 10 seconds.

Example 2

Different combinations of poloxamer 188, a viscosity modifier, and smectite clay were tried in half factorial design and evaluated for suspendability, re-dispersibility, viscosity.

12 individual laboratory scale batches as below were prepared to determine the effect of the composition of poloxamer, smectite clay and/or a viscosity modifier on the uniformity, suspendability, and re-dispersibility of cenobamate. The type and concentration of a viscosity modifier, smectite clay, and the concentration of poloxamer 188 were varied according to the Table 2. The remaining formulation components were fixed as presented in Table 3.

TABLE 2

(unit: mg/mL)

| Formulation No. | Poloxamer 188 | Avicel RC591 | Xanthan Gum | HPMC E5M | Veegum HV |
|---|---|---|---|---|---|
| 1 | 1.00 | 10.00 | — | — | 0.00 |
| 2 | 0.10 | 10.00 | — | — | 5.00 |
| 3 | 0.10 | 20.00 | — | — | 0.00 |
| 4 | 1.00 | 20.00 | — | — | 5.00 |
| 5 | 0.55 | 15.00 | — | — | 2.50 |
| 6 | 0.55 | — | 3.00 | — | 2.50 |
| 7 | 1.00 | — | 1.00 | — | 0.00 |
| 8 | 0.10 | — | 1.00 | — | 5.00 |
| 9 | 1.00 | — | 5.00 | — | 5.00 |
| 10 | 0.10 | — | 5.00 | — | 0.00 |
| 11 | 0.00 | 13.00 | — | 2.50 | — |
| 12 | 0.55 | 15.00 | 1.00 | — | — |

TABLE 3

Fixed formulation components and composition

| | Ingredient | mg/mL |
|---|---|---|
| 1 | Cenobamate | 10.00 |
| 2 | Avicel RC591/Xanthan Gum/HPMC | Vary according to Table 2 |
| 3 | Veegum HV | Vary according to Table 2 |
| 4 | Poloxamer 188 | Vary according to Table 2 |
| 5 | Citric Acid Monohydrate | 4.30 |
| 6 | Sodium Citrate Dihydrate | 1.80 |
| 7 | Sodium Benzoate | 3.00 |
| 8 | Methylparaben Sodium | 1.40 |
| 9 | Sucralose | 3.00 |
| 10 | Sorbitol | 15.00 |
| 11 | Grape Flavor | 2.00 |
| 12 | Bitter Masker | 1.00 |
| 13 | Water | 967.50 |
| | Total | Vary according to Table 2 |

The uniformity, suspendability, and re-dispersibility were measured by the following procedures:

Uniformity

1. Shook the bottle by hand.
2. Inverted and inspected the bottom of the bottle for caking. If the sample formed a cake it was noted when executing analytical analysis.
3. Using a syringe and canula, obtained a sample from the top and bottom of the bottle for assay of cenobamate and diluted for analytical analysis as per the test method.
4. Compared the results from the top and bottom of the bottle to determine the absolute difference for uniformity.

Suspendability

1. After sampling for uniformity the bottle was sealed and allowed to stand undisturbed.
2. Without shaking or otherwise mixing the sample, obtained an additional aliquot for assay of cenobamate from the bottom of the bottle.
3. Diluted for analytical analysis as per the method.
4. Compared this result to the bottom assay for uniformity to determine the absolute difference for suspendability.

Re-dispersibility

1. Shook the sample by hand for and immediately transferred to a conical tube.
2. Centrifuged the sample.
3. Removed the sample from the centrifuge and shook by hand.
4. Collected a sample for assay from center of the tube.
5. Compared these results to the average assay to determine the percent re-dispersibility.

The measurement of viscosity and any correlation with the suspendability and re-dispersibility would be expected based on Stokes law of terminal velocity of a sphere falling in fluid. From the data in Table 4, the formulations showed acceptable physical stability. Overall, the average uniformity of the various formulations was found to range from 91.1 to 100.8, and the absolute difference (%) was 0.0 to 3.9 for the formulations that were short listed from the entire experimental design.

TABLE 4

| Formulation No. | Suspendability | | Re-dispersibility | |
|---|---|---|---|---|
| | Assay | % ABS diff | Assay | % disp. |
| 1 | 101.3 | 0.6 | 37.2 | 36.9 |
| 2 | 94.5 | 3.7 | 87.7 | 96.3 |
| 3 | 96.4 | 1.0 | 28.9 | 29.7 |
| 4 | 100.1 | 0.5 | 98.6 | 98.0 |
| 5 | 100.9 | 0.3 | 70.8 | 70.4 |
| 6 | 100.3 | 0.6 | 90.8 | 90.0 |
| 7 | 104.6 | 3.6 | 24.2* | 24.0 |
| 8 | 102.4 | 2.0 | 94.7 | 94.4 |
| 9 | 100.8 | 0.0 | 100.7 | 100.0 |
| 10 | 101.4 | 0.7 | 89.1 | 88.5 |
| 11 | 98.5 | 0.1 | 74.2 | 75.3 |
| 12 | 104.4 | −4.2 | 47.9 | 47.8 |

ABS: Absolute
*the value for Re-dispersibility in Formulation 7 was found to be a potential outlier based statistical analysis of the data

Example 3

Based on the results from Examples 1 and 2, the formulations were prepared as shown in Table 5.

TABLE 5

(Unit: mg/mL)

| Ingredient | Formulation I | Formulation II |
|---|---|---|
| Cenobamate | 10.00 | 10.00 |
| Avicel RC591 | 18.00 | 12.00 |
| Veegum HV | 5.00 | 5.00 |
| Poloxamer 188 | 1.00 | 0.25 |
| Citric Acid Monohydrate | 4.30 | 4.30 |
| Sodium Citrate Dihydrate | 1.80 | 1.80 |
| Sodium Benzoate | 3.00 | 3.00 |
| Methylparaben Sodium | 1.40 | 1.40 |
| Sucralose | 3.00 | 3.00 |
| Sorbitol | 15.00 | 15.00 |
| Grape Flavor | 2.00 | 2.00 |
| Bitter Masker | 1.00 | 1.00 |
| Water | 800.00 | 800.00 |
| QS Water | 154.50 | 161.25 |
| Total | 1020.00 | 1020.00 |

Note:
All calculations are based on a density: 1.02 g/mL and pH 4.2

Example 4

Stability of Formulations I and II was evaluated by testing for pH, assay of cenobamate, suspendability, content of related compounds, dissolution, particle size, and XRD. The formulations (upright and inversed) were stored at 25° C./60% RH for twelve months and 40° C./75% RH chambers for six months.

The assay of cenobamate and related compounds was measured using an HPLC method. The suspendability was measured as in Example 2. The dissolution test was performed by the USP Apparatus 2 (paddles, 900 mL, 75 rpm, 37° C., 5 to 45 mins). The particle size was measured by Mie scattering method.

The results show that Formulations I and II (upright/inverted) were stable for at least 6 months in 25° C./60% RH and 40° C./75% RH condition and were stable for twelve months at 25° C./60% RH. The stability results for inverted condition which represents more interaction of the formulation with packaging are provided.

TABLE 6

Stability results for Formulation I (inverted) at 25° C./60% RH

| | Stability Intervals (month) | | | | | |
|---|---|---|---|---|---|---|
| Test | 0 | 1 | 3 | 6 | 9 | 12 |
| pH | 4.2 | 4.5 | 4.6 | 4.7 | 4.8 | 4.8 |
| Assay of Cenobamate (%) | 100.1 | 99.8 | 97.1 | 100.1 | 100.0 | 103.0 |
| Suspendability | Assay: 99.9% Abs. Diff: 0.2% | Assay: 100.0% Abs. Diff: 0.2% | Assay: 98.9% Abs. Diff: 1.8% | Assay: 100.1% Abs Diff: 0.0% | Assay: 100.6% Abs Diff: 0.6% | Assay: 98.9% Abs Diff: 4.1% |
| Related compounds | RRT1.30: 0.05% Total: 0.05% | RRT 0.169: 0.06% Total: 0.06% | RRT 0.169: 0.06% RRT 1.30: 0.05% Total: 0.11% | RRT 0.169: 0.06% Total: 0.06% | RRT 0.112: 0.05% RRT 0.169: 0.09% Total: 0.14% | RRT 0.169: 0.06% Total: 0.06% |
| Dissolution at 15 min (%) | 97% | 93% | 93% | 100% | 99% | 94% |
| Particle Size | D10: 1.6 D50: 4.4 D90: 13.5 | D10: 1.6 D50: 4.4 D90: 13.5 | D10: 2.0 D50: 5.9 D90: 15.4 | D10: 2.4 D50: 6.4 D90: 18.7 | D10: 2.2 D50: 6.0 D90: 15.3 | D10: 1.5 D50: 4.4 D90: 14.4 |
| XRD | Conforms | NT | NT | Conforms | NT | NT |

ND = None Detected,
N/A = Not Applicable,
NT = Not Tested,
Abs. Diff.: Absolute difference from assay value,
RRT: Relative retention time

TABLE 7

Stability results for Formulation I (inverted) at 40° C./75% RH

| | Stability Intervals (month) | | | |
|---|---|---|---|---|
| Test | 0 | 1 | 3 | 6 |
| pH | 4.2 | 4.6 | 4.7 | 4.8 |
| Assay of Cenobamate (%) | 100.1 | 95.7 | 101.3 | 99.2 |
| Suspendability | Assay: 99.9% Abs. Diff: 0.2% | Assay: 98.8% Abs. Diff: 3.1% | Assay: 100.4% Abs Diff: 0.9% | Assay: 99.4% Abs Diff: 0.2% |

TABLE 7-continued

Stability results for Formulation I (inverted) at 40° C./75% RH

| Test | Stability Intervals (month) | | | |
|---|---|---|---|---|
| | 0 | 1 | 3 | 6 |
| Related compounds | RRT1.30: 0.05%<br>Total: 0.05% | RRT0.169: 0.06%<br>Total: 0.06% | RRT0.169: 0.11%<br>YKP3158: 0.07%<br>RRT 1.30: 0.05%<br>Total: 0.23% | RRT 0.169: 0.10%<br>YKP3158: 0.05%<br>Total: 0.15% |
| Dissolution (%) | 97 | 91 | 92 | 97 |
| Particle Size | D10: 1.6<br>D50: 4.4<br>D90: 13.5 | D10: 1.6<br>D50: 4.4<br>D90: 13.4 | D10: 2.1<br>D50: 5.9<br>D90: 15.9 | D10: 2.2<br>D50: 6.2<br>D90: 17.0 |
| XRD | Conforms | NT | NT | Conforms |

ND = None Detected,
N/A = Not Applicable,
NT = Not Tested,
Abs. Diff.: Absolute difference from assay value,
RRT: Relative retention time

TABLE 8

Stability results for Formulation II (inverted) at 25° C./60% RH

| | Stability Intervals (month) | | | | | |
|---|---|---|---|---|---|---|
| | 0 | 1 | 3 | 6 | 9 | 12 |
| pH | 4.2 | 4.5 | 4.7 | 4.8 | 4.8 | 4.8 |
| Assay of Cenobamate (%) | 98.7% | 100.1% | 97.0% | 98.9% | 98.3% | 101.5% |
| Suspendability | Assay: 98.2%<br>Abs. Diff: 0.5% | Assay: 100.3%<br>Abs. Diff: 0.2% | Assay: 95.7%<br>Abs. Diff: 1.3% | Assay: 98.6%<br>Abs. Diff: 0.3% | Assay: 97.2%<br>Abs Diff: 1.2% | Assay: 98.6%<br>Abs Diff: 2.9% |
| Related compounds | RRT1.30: 0.05%<br>Total: 0.05% | ND | RRT 0.169: 0.06%<br>RRT1.30: 0.05%<br>Total: 0.11% | RRT 0.169: 0.06%<br>RRT1.30: <LOQ<br>Total: 0.06% | RRT 0.169: 0.08%<br>Total: 0.08% | RRT 0.169: 0.08%<br>Total: 0.08% |
| Dissolution (%) | 96% | 95% | 98% | 98% | 97% | 97% |
| Particle Size | D10: 1.5<br>D50: 4.2<br>D90: 13.0 | D10: 1.5<br>D50: 4.2<br>D90: 13.0 | D10: 2.0<br>D50: 5.5<br>D90: 13.8 | D10: 2.3<br>D50: 6.2<br>D90: 15.4 | D10: 2.2<br>D50: 5.9<br>D90: 15.0 | D10: 1.6<br>D50: 4.3<br>D90: 13.4 |
| XRD | Conforms | NT | NT | Conforms | NT | NT |

ND = None Detected,
N/A = Not Applicable,
NT = Not Tested,
Abs. Diff.: Absolute difference from assay value,
RRT: Relative retention time

TABLE 9

Stability results for Formulation II (inverted) at 40° C./75% RH

| | Stability Intervals (month) | | | |
|---|---|---|---|---|
| | 0 | 1 | 3 | 6 |
| pH | 4.2 | 4.7 | 4.8 | 4.9 |
| Assay of Cenobamate (%) | 98.7 | 94.7 | 96.8 | 99.2 |
| Suspendability | Assay: 98.2%<br>Abs. Diff: 0.5% | Assay: 98.1%<br>Abs. Diff: 3.4% | Assay: 96.1%<br>Abs. Diff: 0.7% | Assay: 99.4%<br>Abs. Diff: 0.2% |
| Related compounds | RRT1.30: 0.05%<br>Total: 0.05% | RRT 0.169: 0.07%<br>Total: 0.07% | RRT 0.169: 0.11%<br>YKP3158: 0.09%<br>Total: 0.20% | RRT 0.169: 0.10%<br>YKP3158: 0.06%<br>Total: 0.16% |

TABLE 9-continued

Stability results for Formulation II (inverted) at 40° C./75% RH

| | Stability Intervals (month) | | | |
|---|---|---|---|---|
| | 0 | 1 | 3 | 6 |
| Dissolution (%) | 96% | 94% | 98% | 98% |
| Particle Size | D10: 1.5 | D10: 1.6 | D10: 2.0 | D10: 2.2 |
| | D50: 4.2 | D50: 4.4 | D50: 5.5 | D50: 6.2 |
| | D90: 13.0 | D90: 13.3 | D90: 13.8 | D90: 17.0 |
| XRD | Conforms | NT | NT | Conforms |

ND = None Detected,
N/A = Not Applicable,
NT = Not Tested,
Abs. Diff.: Absolute difference from assay value,
RRT: Relative retention time Formulation I and II were stable for 12 months at 25° C./60% RH and 6 months at 40° C./75% RH.

What is claimed is:

1. An aqueous formulation comprising a carbamate compound of Formula 1, or a pharmaceutically acceptable salt, solvate or hydrate thereof, poloxamer, and an aqueous carrier:

[Formula 1]

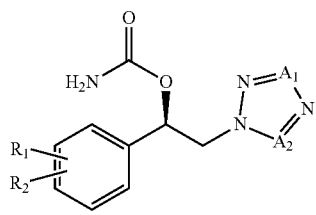

wherein,
$R_1$ and $R_2$ are each independently selected from the group consisting of —H, halo, $C_1$-$C_8$ alkyl, halo-$C_1$-$C_8$ alkyl, $C_1$-$C_8$ thioalkoxy, and $C_1$-$C_8$ alkoxy; and
one of $A_1$ and $A_2$ is CH, and the other is N,
wherein the aqueous formulation is in the form of a suspension formulation.

2. The aqueous formulation according to claim 1, wherein $R_1$ and $R_2$ are each independently selected from the group consisting of —H, halo, and $C_1$-$C_8$ alkyl.

3. The aqueous formulation according to claim 1, wherein the carbamate compound of Formula 1 is carbamic acid (R)-1-(2-chlorophenyl)-2-tetrazol-2-yl-ethyl ester.

4. The aqueous formulation according to claim 1, which contains the carbamate compounds of Formula 1 in a concentration of about 1 mg/ml to about 100 mg/ml.

5. The aqueous formulation according to claim 1, wherein the poloxamer is an ABA block type copolymer which consists of 75 to 85% poly(ethyleneoxide) (PEO) units and 15 to 25% poly(propylene oxide) (PPO) units.

6. The aqueous formulation according to claim 1, wherein the poloxamer is an ABA block type copolymer which consists of about 80% PEO units and about 20% PPO units.

7. The aqueous formulation according to claim 6, wherein the poloxamer is poloxamer 188.

8. The aqueous formulation according to claim 1, which contains the poloxamer in a concentration of about 0.1 mg/ml to about 1.5 mg/ml.

9. The aqueous formulation according to claim 1, which further comprises smectite clay.

10. The aqueous formulation according to claim 9, wherein the smectite clay is selected from the group consisting of aluminum silicate, magnesium aluminum silicate, sodium magnesium silicate, organically modified smectite, and a mixture thereof.

11. The aqueous formulation according to claim 9, which contains the smectite clay in a concentration of about 2.5 mg/ml to about 7.0 mg/ml.

12. The aqueous formulation according to claim 1, which further comprises a viscosity modifier.

13. The aqueous formulation according to claim 12, wherein the viscosity modifier is selected from the group consisting of cellulose or a derivative thereof, and xanthan gum.

14. The aqueous formulation according to claim 13, wherein the cellulose derivative is selected from the group consisting of methyl cellulose (MC), ethyl cellulose (EC), hydroxyethylcellulose (HEC), hydroxypropyl cellulose (HPC), hydroxypropyl methylcellulose (HPMC), carboxymethyl cellulose (CMC), microcrystalline cellulose (MCC), cellulose acetate (CA), cellulose acetate phthalate (CAP), cellulose acetate butyrate (CAB), cellulose acetate trimelitate (CAT), hydroxupropylmethyl cellulose phthalate (HPMCP), and a combination thereof.

15. The aqueous formulation according to claim 12, which contains the viscosity modifier in a concentration of about 1 mg/ml to about 25 mg/ml.

16. The aqueous formulation according to claim 13, which contains the xanthan gum in a concentration of less than about 1 mg/ml to about 10 mg/ml.

17. The aqueous formulation according to claim 13, which contains the cellulose or derivative thereof in a concentration of about 5 mg/ml to about 14 mg/ml.

18. The aqueous formulation according to claim 13, which contains the cellulose or derivative thereof in a concentration of about 15 mg/ml to about 25 mg/ml.

19. The aqueous formulation according to claim 1, which further comprises at least one selected from the group consisting of a recrystallization inhibitor, a flavor, a bitter masker, a preservative, and a buffer.

20. The aqueous formulation according to claim 19, wherein the recrystallization inhibitor is polyvinylpyrrolidone (PVP) or hydroxypropyl methylcellulose (HPMC).

21. The aqueous formulation according to claim 20, which contains PVP in a concentration of about 20 mg/ml to about 40 mg/ml.

22. The aqueous formulation according to claim 20, which contains HPMC in a concentration of about 1 mg/ml to about 5 mg/ml.

23. The aqueous formulation according to claim 19, wherein the buffer is a citrate buffer or a phosphate buffer.

24. The aqueous formulation according to claim 1, which has a pH of 3.5 to 5.5.

25. The aqueous formulation according to claim 1, wherein the aqueous carrier is water, or a mixture of water and a water-miscible organic solvent.

26. The aqueous formulation according to claim 1, wherein the compound of Formula 1 to be used to prepare the aqueous formulation has a D90 of 10 to 20 μm, 20 to 30 μm, 30 to 40 μm, 40 to 50 μm, 50 to 60 μm, 60 to 70 μm, 70 to 80 μm, 80 to 90 μm, or 90 to 100 μm.

27. The aqueous formulation according to claim 1, which is a formulation for oral administration.

28. The aqueous formulation according to claim 1, which comprises about 8 mg/ml to 12 mg/ml cenobamate, about 0.1 mg/ml to about 1.5 mg/ml poloxamer, about 2.5 mg/ml to about 7.0 mg/ml smectite clay, and water.

29. An aqueous formulation comprising a carbamate compound of Formula 1, or a pharmaceutically acceptable salt, solvate or hydrate thereof, smectite clay, and an aqueous carrier:

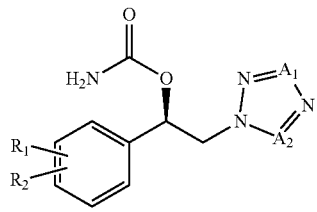

[Formula 1]

wherein, $R_1$ and $R_2$ are each independently selected from the group consisting of —H, halo, $C_1$-$C_8$ alkyl, halo-$C_1$-$C_8$ alkyl, $C_1$-$C_8$ thioalkoxy, and $C_1$-$C_8$ alkoxy; and one of $A_1$ and $A_2$ is CH, and the other is N, wherein the aqueous formulation is in the form of a suspension formulation.

30. The aqueous formulation according to claim 19, which contains preservative in a concentration of about 0.5 mg/ml to about 5.0 mg/ml.

* * * * *